US012661088B2

(12) United States Patent
Lee

(10) Patent No.: US 12,661,088 B2
(45) Date of Patent: Jun. 23, 2026

(54) CONNECTION FOR A MULTI-DIMENSIONAL MATRIX TRANSDUCER

(71) Applicant: Siemens Medical Solutions USA, Inc., Malvern, PA (US)

(72) Inventor: Baik Woo Lee, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 769 days.

(21) Appl. No.: 18/149,683

(22) Filed: Jan. 4, 2023

(65) Prior Publication Data

US 2024/0215951 A1     Jul. 4, 2024

(51) Int. Cl.
*A61B 8/00*          (2006.01)

(52) U.S. Cl.
CPC .......... *A61B 8/4483* (2013.01); *A61B 8/4494* (2013.01)

(58) Field of Classification Search
CPC ........................... A61B 8/4483; A61B 8/4494
See application file for complete search history.

(56) References Cited

U.S. PATENT DOCUMENTS

| | | | |
|---|---|---|---|
| 8,169,125 B2 | 5/2012 | Savord et al. |
| 8,659,212 B2 | 2/2014 | Eggen et al. |
| 8,742,646 B2 | 6/2014 | Wodnicki et al. |
| 9,180,490 B2 | 11/2015 | Tai |
| 2008/0273424 A1 | 11/2008 | Wodnicki et al. |
| 2008/0315724 A1 | 12/2008 | Kunkel, III |
| 2011/0071397 A1 | 3/2011 | Wodnicki et al. |
| 2021/0138506 A1 | 5/2021 | Lee et al. |
| 2022/0018957 A1 | 1/2022 | Lee |
| 2022/0146669 A1 | 5/2022 | Simpson et al. |

FOREIGN PATENT DOCUMENTS

| | | |
|---|---|---|
| WO | 2015041780 A2 | 3/2015 |

*Primary Examiner* — Emily P Pham
*Assistant Examiner* — Monica Mata

(57) ABSTRACT

For transducers with a chip-on-array arrangement, the dematching layer extends beyond a footprint of the array, allowing for connection of the grounding plane without sidewall metalization. The flexible circuit material is tiled, reducing thermal deformation, reducing cost, and increasing process yield. The dematching layer extension and the tiled flexible circuit may be used together or individually in a given transducer.

14 Claims, 5 Drawing Sheets

2nd acoustic matching layer 100
1st acoustic matching layer 120
Piezoelectric layer 130
Conductive ground return layer 150
Dematching layer (WC) 140
Flex circuit 160
ASIC electrical joints 175

ASIC 170 ASIC 170

Acoustic backer 180

Slit in flex circuits
400

500 — Bond Tiles of Flex to Dematching Layer

510 — Attach Chip to Flex

520 — Stack Array on Dematching Layer

530 — Lay Ground Plane

540 — Connect Ground Plane to Dematching Layer

Bonding layer

140

Flex circuit 160

Dematching layer (WC) 140

Flex circuit 160

ASIC 170

ASIC electrical joints
175

1st acoustic matching layer 120

Piezoelectric layer 130

Dematching layer (WC) 140

Flex circuit 160

ASIC 170

ASIC electrical joints 175

Singulation 190

1st acoustic matching layer 120

Piezoelectric layer 130

Dematching layer (WC) 140

Flex circuit 160

ASIC 170

ASIC electrical joints 175

Conductive ground return layer 150

1st acoustic matching layer 120

Piezoelectric layer 130

Dematching layer (WC) 140

Flex circuit 160

ASIC electrical joints 175

ASIC 170

2nd acoustic matching layer 100

Conductive ground return layer 150

1st acoustic matching layer 120

Piezoelectric layer 130

Dematching layer (WC) 140

Flex circuit 160

ASIC electrical joints 175

ASIC 170

CONNECTION FOR A MULTI-DIMENSIONAL MATRIX TRANSDUCER

BACKGROUND

The present embodiments relate to interconnection of transducer arrays with electronics. A typical ultrasound imaging system has a limited number of channels (e.g., 64 to 256 channels) determined by the number of cables through which the system communicates with ultrasound transducers. Since two-dimensional (2D) matrix ultrasound transducers may have more elements (e.g., over tens of thousands of acoustic elements) than the system channels, micro-beamforming application specific integrated chips (ASICs) placed as close to the acoustic elements as possible directly operate acoustic elements. For chip-on-array (COA), one or more ASICs placed underneath diced acoustic elements directly drive the acoustic elements individually or in small groups for various beamforming. To connect the ASICs, less desirable low temperature connections may be used to avoid problems caused by application of heat to the laminated stack of the acoustic elements. The cost for the flexible circuit to route all the element signals may be high and have poor process yield. To connect the ground from the PZT layer to the ASICs, sidewall metalization of the PZT is used. This metalization results in a limited thickness of the connection, increasing undesired resistance, and is prone to break.

SUMMARY

By way of introduction, the preferred embodiments described below include methods, systems and components for transducers with COA. The dematching layer extends beyond a footprint of the array, allowing for connection of the grounding plane without sidewall metalization. The flexible circuit material is tiled, reducing thermal deformation, reducing cost, and increasing process yield. The dematching layer extension and the tiled flexible circuit may be used together or individually in a given transducer.

In a first aspect, a multidimensional transducer array system is provided. An acoustic array has transducer elements distributed in a grid over two dimensions in a first area. A dematching layer is adjacent to the acoustic array. The dematching layer has a second area greater than the first area such that at least a first portion extends beyond a footprint of the acoustic array. The dematching layer being electrically conductive. A ground return layer is adjacent to the acoustic array on a side opposite the dematching layer. The ground return layer extends to the dematching layer. A flexible circuit material layer is adjacent to the dematching layer. The flexible circuit material is separated into multiple tiles. An integrated circuit chip connects with the flexible circuit material layer. A ground path connects from the integrated circuit chip, through the flexible circuit material layer, and through the dematching layer to the ground return layer.

In one embodiment, the transducer elements separately electrically connect to the integrated circuit chip through kerfed portions of the dematching layer and vias in the flexible circuit material layer. In another embodiment, the integrated circuit chip is an application specific integrated circuit flip chip mounted to the flexible circuit material layer. As yet another embodiment, the transducer elements are separated by kerfs and each includes a matching layer, a piezoelectric, a kerfed portion of the dematching layer, and a signal electrode. The ground return layer is free of kerfs and is adjacent to the matching layer.

According to an embodiment, the ground return layer is a metal sheet that bends at an edge of the acoustic array to connect with the first portion of the dematching layer extending beyond the footprint of the acoustic array. In one example, the dematching layer has the first portion and a second portion extending beyond the footprint of the acoustic array. The metal sheet connects with both the first and second portions of the dematching layer. Alternatively, the ground return layer is a polymer layer (e.g, mylar) coated with thin metal (e.g., metal sheet in a laminate or supported by other material).

In an embodiment, the dematching layer is tungsten carbide.

In other embodiments, the flexible circuit material is separated into multiple tiles as separate sheets in a same plane or as a sheet having slits formed therein.

In a second aspect, a transducer array system is provided. Transducer elements are in an array. A ground layer is distributed over the transducer elements of the array. An integrated circuit chip electrically connects to the transducer elements. A dematching layer is between the array and the integrated circuit chip. The dematching layer is electrically conductive and has a portion not covered by array. The ground layer extends from over the transducer elements of the array to the portion of the dematching layer not covered by the array.

According to an embodiment, the dematching layer is tungsten carbide.

As another embodiment, the array has a first area in a plane parallel to an acoustic face. The dematching layer has a second area parallel with the plane. The second area larger than the first area by an area of the portion.

In another embodiment, the ground layer is a metal sheet that bends at an edge of the array to connect to the dematching layer.

In a further embodiment, a sheet of flexible circuit material is between the dematching layer and the integrated circuit chip. The sheet is separated into two or more tiles such that different tiles electrically connect to different ones of the transducer elements.

In a third aspect, a method is provided for forming an acoustic transducer. Tiles of flexible circuit material are bonded to a dematching layer. A semiconductor chip is attached to the flexible circuit material. The attachment uses application of heat. An array of transducer elements is stacked on the dematching layer.

In one embodiment, separate sheets of the flexible circuit material in a same plane are bonded to different parts of the dematching layer.

According to an embodiment, a sheet of the flexible circuit material is bonded to the dematching layer. The sheet has slits forming the tiles.

In another embodiment, the semiconductor chip attaches to the flexible circuit material after the bonding of the tiles of the flexible circuit material to the dematching layer. The application of heat is from solder reflow or anisotropic conductive film thermal compression bonding.

As yet another embodiment, the array is stacked on the dematching layer where the dematching layer has a larger surface area on a first surface than an area of the largest surface of the array such that the dematching layer extends beyond the array. A ground plane is laid on the array and connected to the dematching layer outside a footprint of the largest surface of the array.

The present invention is defined by the following claims, and nothing in this section should be taken as a limitation on these claims. Further aspects and advantages of the invention are discussed below in conjunction with the preferred embodiments and may be later claimed independently or in combination. Different embodiments may achieve or fail to achieve different objects or advantages.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A 2D matrix ultrasound transducer has various aspects to improve COA technology. An easier ground return path is provided in 2D matrix transducer. The dematching layer has an extended footprint relative to the array of transducer elements, allowing the ground plane to connect to the dematching layer instead of using metalized sidewalls. To enable high temperature ASIC attachment with improved reliability and to integrate flex circuits in a cost-effective way, tiled flexible circuit material is used. Better process yield and design freedom are provided.

Various matrix transducers, such as transthoracic echo (TTE) transducer, transesophageal echocardiography (TEE) transducer, catheter transducer, or other ultrasound transducers using COA with lowest parasitic may use the tiling or extended dematching.

Figure 1:
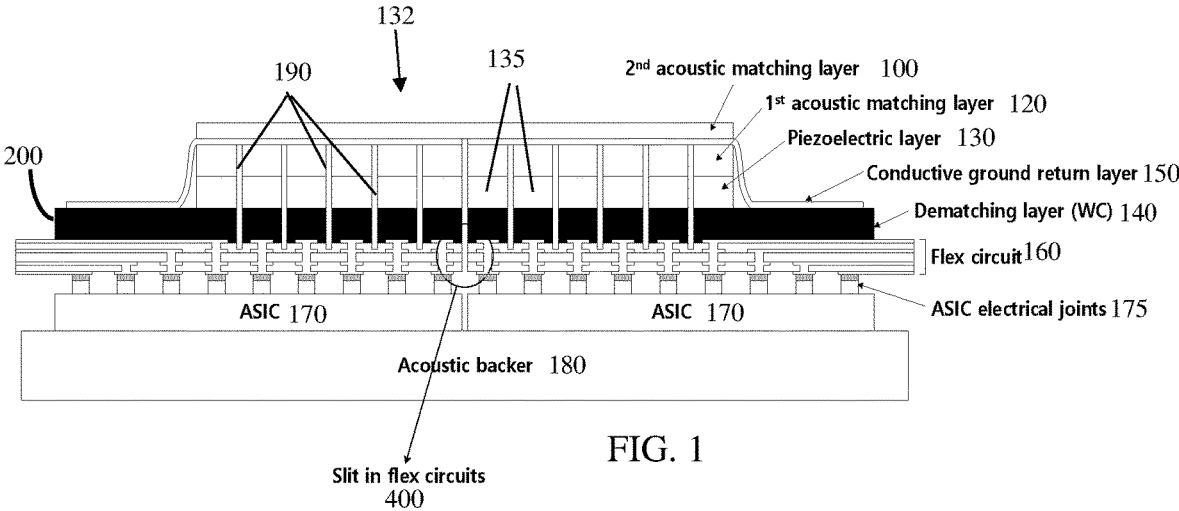
FIG. 1 is a cross-section view of one embodiment of a multidimensional transducer array system.

FIG. 1 is a cross-section view of one embodiment of a transducer array system. The cross-section is in the depth-elevation dimension where depth is vertical on the drawing and elevation is horizontal on the drawing.

The system is used for an ultrasound transducer probe, such as in a handheld probe for scanning from an exterior of a patient or an intra-cavity (e.g., TEE or TTE) or catheter-based probe for scanning from within a patient. The system includes a one or multi-dimensional transducer array, such as a matrix array with a distribution of elements 135 in both azimuth and elevation. A multidimensional transducer array system may be provided.

The array system includes matching layers 100, 120, a ground layer 150, an array layer (e.g., piezoelectric layer 130), a dematching layer 140, flexible circuit material layer 160, chips 170 (e.g., application specific integrated circuits), and an acoustic backer 180. Additional, different, or fewer layers may be included, such as not including the acoustic backer 180, the chips 170, and/or the second matching layer 100. In one example, a lens and/or housing is provided around the transducer system or adjacent to the second acoustic matching layer 100. In other examples, the flexible circuit material layer 160 is provided without the dematching layer 140 or vise versa.

Figure 5:
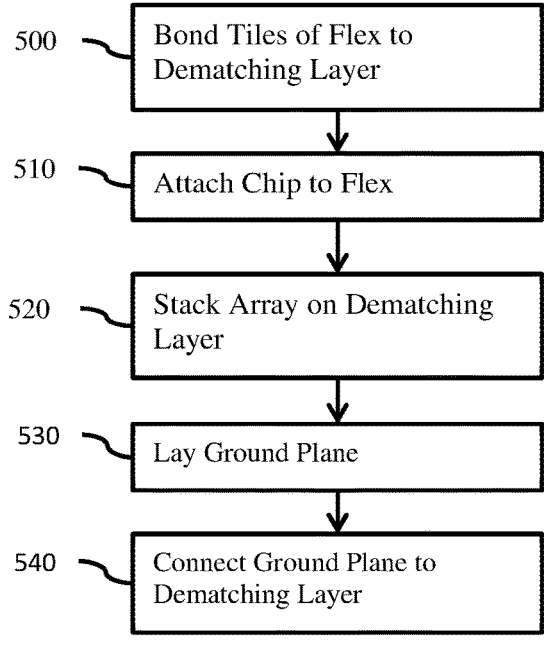
FIG. 5 is a flow chart diagram of one embodiment of a method for forming an acoustic transducer using an extended dematching layer and/or tiled flexible circuit material.

The array system and corresponding probe are formed using the method of FIG. 5 or another method.

The matching layers 100 and 120 are % wavelength thickness layers of material. Multiple layers for a gradual change in acoustic impedance may be used, but only one matching layer is provided in other embodiments. The second matching layer 100 provides a transition in acoustic impedance between the patient, lens, or other material and the first matching layer 120. Similarly, the first matching layer 120 provides an acoustic impedance transition from the second matching layer 100 to the piezoelectric or other transducer array layer 130. In one example, the second matching layer 100 is a urethane or other material with or without filler. The first matching layer 120 is graphite or other conductive material. The graphite may be impregnated with copper or other metal for enhanced conductivity.

The array layer is shown as a PZT layer 130 but may include the first matching layer 120 and/or the dematching layer 140. The PZT layer 130 is a slab or plate of PZT material. A solid PZT may be used. Single or poly-crystal PZT material may be used. In other embodiments, a composite of piezoelectric and epoxy or another polymer is used. Microelectromechanical (capacitive membrane) elements 135 may be used instead of PZT. Piezoelectric examples are used herein, so the array layer will be referenced to the PZT layer 130.

The multidimensional transducer array 132 is an array of PZT elements 135. Kerfs 190 separate the elements 135 of the PZT layer 130. The kerfs 190 also separate the first acoustic matching layer 120 and the dematching layer 140. In other embodiments, the kerfs 190 separate the second matching layer 100. In yet other embodiments, the kerfs 190 do not extend through the dematching layer 140 and/or the first acoustic matching layer 120. The kerfs 190 may be in a grid pattern as viewed from an acoustic face of the transducer, such as forming separate elements 135 in elevation and azimuth directions. The array layer includes elements 135 that transduce between acoustic and electrical energies, such as an array of transducer elements 135 formed from PZT material. The transducer elements 135 of the array layer are distributed in a grid over one or two dimensions.

The array is flat, concave, or convex. In one embodiment, the elements 135 are distributed along two dimensions. The elements 135 are distributed along any of various pitches, such as every 150, 250, 400 or 500 micrometers, in a fully sampled spacing along two dimensions (e.g., azimuth and elevation). Full or sparse sampling of placement of the elements 135 is provided.

Each of the transducer elements 135 of the array includes at least two electrodes. The conductive ground return layer 150 provides one of the electrodes. The other electrodes are separated by the kerfs 190 with the PZT layer 130, such as being electrodes deposited on the PZT layer 130 or the conductive singulated parts of the dematching layer 140. The elements 135 transduce between electrical and acoustical energies. The ground layer 150 defines a 0 volt or ground signal. The electrical energy generated by the PZT or provided to the PZT is provided on an electrode opposite the ground layer 150. This signal electrode is separate for each element 135, providing a separate conductive path from the PZT layer 130 and through the dematching layer 140 to the flexible circuit material layer 160. Since the kerfs 190 extend through the dematching layer 140, different individual parts of the dematching layer 140 form part of the electrically conductive path for the signals.

Due to the full ground layer 150 covering the elements 135 of the PZT layer 130, the kerfs 190 may be filled with air or another gas. By wrapping the stack with the ground layer 150 and the dematching layer 140 (or flexible circuit material layer 160), air-filled kerfs 190 with better sensitivity as compared to epoxy or another fill may be used. In alternative embodiments, the kerfs 190 are filled with epoxy or another filler.

The array of the PZT layer 130 has a footprint in azimuth and elevation. The largest surface of the PZT layer 130 is in a plane normal to the direction of transmit and receive, such as a plane defining an acoustic face of the array. The elements 135 are distributed over this plane parallel to the acoustic face, resulting in an area defining the footprint of the array. A curved or convex surface for distribution of the elements in azimuth and elevation may be used.

The dematching layer 140 is a ¼, ⅛, 1/16 or another wavelength thickness layer of material. Any material may be used, such as tungsten carbide (WC) or graphite. The dematching layer 140 provides a clamped boundary condition, leading to better sensitivity and wider bandwidth in the ultrasound transducer. The dematching layer 140 is between the array (PZT layer 130) and the integrated circuit chip (170).

The dematching layer 140 is electrically conductive. The material of the layer itself may be conductive and/or filler or composite is added to provide conductivity. The dematching layer 140 is used to form a common ground connection for the 2D matrix transducer. To drive the PZT elements 135, the ground return path is completed by connecting the top electrode (ground layer 150) of all the singulated acoustic elements 135 to the electrical ground of ultrasound system. The ground layer 150 is connected to the system ground. In an alternative embodiment, a metallization coating on the sidewall of outermost acoustic elements 135 of the array is used. This metalization coating may result in high electrical resistance in the ground path and is prone to break at the sharp corner of piezoelectric layer 130, thus requiring expensive beveling machining at the corner of fragile piezoelectric ceramic layer 130.

Figure 2:
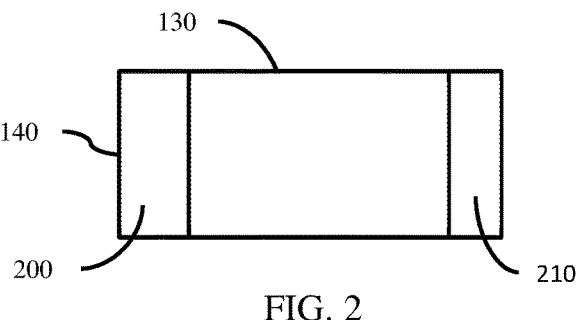
FIG. 2 is a top view of one embodiment of an array on an extended dematching layer.

In one embodiment, the dematching layer 140 is used for the ground connection. The acoustic dematching layer 140 is extended beyond an active acoustic zone. FIG. 2 shows an example. The PZT layer 130 has a footprint defining an area of the acoustic face of the array. This area is defined by the distribution of the transducer elements 135. The dematching layer 140 is sized to extend beyond the footprint of the array. FIG. 2 shows the dematching layer 140 extending beyond the area of the array of the PZT layer 130 on two sides, but only one, three, or all four sides of the dematching layer 140 may extend beyond the array 130 when viewed from above or below (i.e., normal to the largest surface of the array and/or dematching layer 140).

The dematching layer 140 has an area greater than the area of the array such that at least one portion 200, 210 extends beyond a footprint of the acoustic array. The area of the dematching layer 140 parallel with a plane of the array, acoustic face, or average plane through the array is larger than the area of the array by an area of the portion 200, 210.

The parts 200, 210 extending beyond the array or PZT layer 130 form pads for ground connection. The parts or portions 200, 210 of the dematching layer 140 not covered by the array of the PZT layer 130 may be used to connect to the ground layer 150. By extending beyond the active acoustic zone, the ground return layer 150 may terminate on, adjacent to, or against the dematching layer 140. The dematching layer 140 is itself electrically conductive and connects to the electrical ground of the flexible circuit material layer 160 so that a conductive ground path is completed from the top of diced array to the flexible circuit material layer 160 without any sidewall metallization on acoustic elements 135.

The ground layer 150 is a metal foil or sheet. For example, a copper sheet or other conductive material is used. Alternatively, the ground return layer is a polymer layer (e.g., mylar) coated with thin metal.

The ground layer 150 is distributed over the PZT layer and/or one or both matching layers 100, 120. As shown in FIG. 1, the ground layer 150 covers the first matching layer 120 and is covered by the second matching layer 100. The kerfs 190 are formed to separate the transducer elements 135, and then the ground layer 150 without kerfs is laid over the separated transducer elements 135. The ground layer 150 is adjacent (e.g., rests against the elements 135 and/or conductively connected to the PZT layer 130) to the acoustic array on a side opposite the dematching layer 140.

The ground layer 150 is a ground return, so connects to the chip 170 or ultrasound system ground. For this connection, the ground layer 150 extends to the dematching layer 140. The ground layer 150 extends from over the transducer elements 135 of the array to the portion 200, 210 of the dematching layer 140 not covered by the array. The ground layer 150 may have some flexibility. By having extended the conductive dematching layer 140 beyond the footprint of the PZT layer 130 and corresponding array of transducer elements 135, the ground layer 150 may bend over the edge of the array to extend down to and contact or lay on part of the dematching layer 140. At least part of the ground layer 150 extends to and terminates at the extended dematching layer 140. The extension allows the ground layer 150 to contact the dematching layer with less aggressive bending. A thicker ground plane layer 150 than a metalized surface may be used. The metal sheet bends without breaking or tearing at the edge of the acoustic array to connect with the portions 200 and/or 210.

In one embodiment, the metal sheet of the ground layer 150 extends of the entire circumference (e.g., all four edges for a square or rectangular array) to the dematching layer 150 with portions extending beyond the footprint on all (e.g., four) sides. The ground layer 150 is free of kerfs 190. This allows sealing the array so that air is trapped in the kerfs. In the example of FIG. 1, the ground layer 150 extends from two parallel edges on opposite sides of the array of elements 135 and rests on the portions 200, 210. The ground layer 150 connects to the dematching layer 140 on fewer than all sides (e.g., on only 2 sides).

The ground layer 150 connects to the dematching layer 150. Various bonding materials can be used for the termination of the ground return layer 150 on the dematching layer 140. For example, epoxy, silver paste, or anisotropic conductive paste (ACP) bonding is used. The same or different bonding is used to bond the matching layers 100, 120, PZT layer 130, dematching layer 140, and/or flexible circuit material layer 160.

The flexible circuit material layer 160 is a sheet of flexible material on and/or in which traces and/or vias may be formed (e.g., deposition and/or etching). For example, a sheet of polyimide is used. The sheet is positioned between the dematching layer 140 and the chip 170. Passive and/or active electronics may be attached.

The flexible circuit material layer 160 includes a plurality of vias. One via is provided for each transducer element 135, but additional or fewer vias may be provided. Similarly, one or more vias are provided for the ground return (e.g., electrically connecting to the portions 200, 210 of the dematching layer 140 to which the ground layer 150 connects). The vias are formed in the flexible circuit material layer 160, such as by etching, deposition, drilling, or molding. A conductor, such as copper, lines or fills a hole to create a conductive path through a thickness of the flexible circuit material layer 160. These vias, with or without traces, provide an electrically conductive path from one side of the flexible circuit material layer 160 to the other side, such as to allow electrical connection from the signal electrodes of the elements 135 to the chips 170.

A single layer of flexible circuit material is used. In other embodiments, more than one flexible circuit material layer 160 is provided. For example, a stack of two, three, or more layers of flexible circuit material is provided. Internal routing of traces and/or routing on the different layers of flexible circuit material may allow redistribution or change in pitch between the pitch of the array of elements 135 and a pitch of connection pads of the chips 170.

The flexible circuit material layer 160 connects with the acoustic stack to form the acoustic module. Asperity contact is provided from the separated parts of the dematching layer 140 of the elements 135 to traces, vias, or other conductors on and/or in the flexible circuit material layer 160. The signal electrodes (e.g., metalized electrodes on the PZT or the separated portions of the conductive dematching layer 140) connect to separate pads and traces of the flexible circuit material layer 160. The physical connection is by bonding, so a layer of bonding material is provided while still providing the flexible circuit material layer 160 adjacent to the dematching layer 140. The bonding material may be epoxy, Ag paste, or ACP. The flexible circuit material layer 160 is bonded to the acoustic stack or array, such as holding the flexible circuit material 160 to the dematching layer 140.

The flexible circuit material layer 160 is adjacent to the chips 170. One or more chips 170 connect to the flexible circuit material layer 160. Soldering, ACF, or other chip-to-flex connection may be used. For example, solder bumps or balls are provided for soldering pads of the chips 170 adjacent to pads on the flexible circuit material layer 160. The creating of the electrical joints 175 uses heat, such as for solder flow.

To be more resistant to deformation from the heat for attaching the adjacent chips 170 given the rigidity of the adjacent dematching layer 140 opposite the chips 170, the flexible circuit material layer 150 is tiled. The flexible circuit material is separated into multiple (e.g., two, three, four, or more) tiles. With a large number (e.g., hundreds or thousands) of transducer elements 135, the flexible circuit material layer 160 connecting the chips 170 to the acoustic elements 135 is large and complicated with higher circuitry routing and increasing number of vias while the features on the flex circuits are small (small vias and finer line/traces on the flex circuits). It is not economical to use a single large flex circuit for the COA technologies to achieve a larger aperture 2D matrix transducer. Alternatively, tiling is not used. A single sheet or stack of sheets extending of the entire extend of the array is used.

Figure 3:
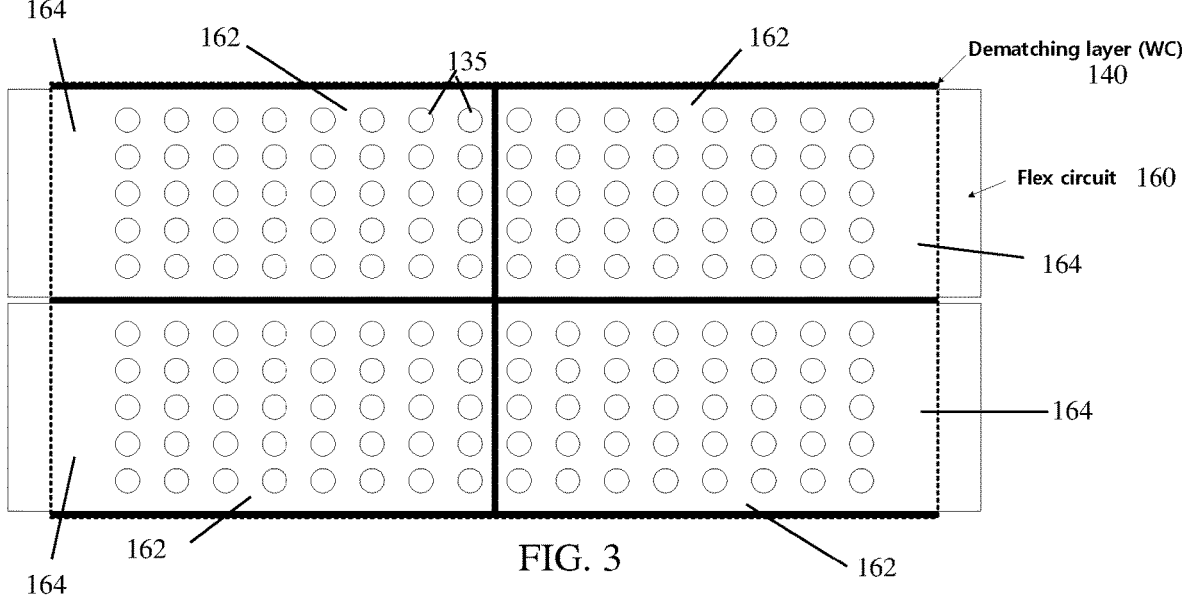
FIGS. 3 and 4 are bottom views showing examples of tiling flexible circuit material.
Figure 4:
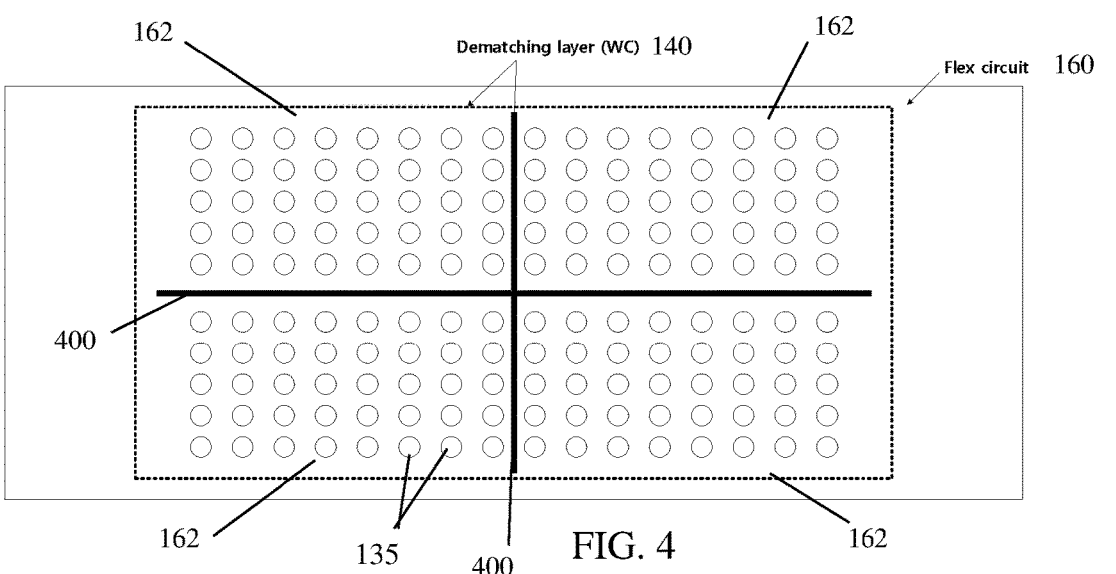

Referring to FIGS. 3 and 4, the flexible circuit material layer 160 is separated into two or more tiles 162 such that different tiles 162 electrically connect to different ones of the transducer elements 135. The separate tiles 162 connect to different groups of the elements 135 (represented by circles), forming four tiles 162 in a same plane or distributed along azimuth and/or elevation.

FIG. 3 shows one embodiment using tiling. Four separate sheets 164 of flexible circuit material form the flexible circuit material layer 160. Each separate sheet 164 is a separate tile 162 of the flexible circuit material layer 160. Separate sheets 164 are provided in a same plane. Multiple small sized flex circuits are tiled over the dematching layer 140 instead of a single large flex circuit. With smaller size of flex circuits, the flex process yield and cost can be improved. Compared to single large flex circuit, the small and tiled flex circuits can further reduce the thermal deformation mismatch between dematching layer 140 and the flexible circuit material layer 160, enabling high temperature process of chip 170 attachment, like solder reflow and ACF thermal compression bonding, which are preferred ASIC interconnections due to their superior reliability. One or more chips 170 are mounted over each of the tiles 162.

FIG. 4 shows another approach for tiling the flexible circuit material layer 160. The flexible circuit material sheet or layer 160 is separated into multiple tiles 162 as a sheet having slits 400 formed therein. Small slits 400 are introduced in the flex circuit material layer 160, which slits 400 minimize thermal deformation mismatch, if any, between the flex circuit material layer 160 and the dematching layer 140 during high temperature process of chip attach like solder reflow and ACF thermal compression bonding. FIG. 4 shows two slits 400 forming a "+" pattern. Other patterns of slits 400 may be used, such as one slit along azimuth or elevation. The slits 400 may be any thickness, such as less (e.g., ½ or ¼) than an element 135 pitch. The slits 400 extend less than an entire length or width of the flexible circuit material layer 160. Alternatively, the slits 400 extend along the entire width or length, creating separate sheets 164. Other tiling may be used. The slits 400 are formed completely through the thickness of the sheet. Slits 400 extending less than a full thickness of the flexible circuit material layer 160 may be used.

One or more integrated circuit chips 170 connect with the flexible circuit material layer 160. The integrated circuit chip 170 is an integrated circuit, such as an application specific integrated circuit (ASIC) as shown in FIG. 1, analog circuit, digital circuit, switch, multiplexer, controller, processor, digital signal processor, field programmable gate array, or other now known or later developed active electrical component. The integrated circuit chip 170 may be in a chip form as an integrated circuit.

The active electrical components are semiconductors, such as transistors devices. "Active" electrical component is used to convey a type of device rather than operation of the device. Transistor-based or switch-based devices are active while resistors, capacitors or inductors are passive devices. The active electrical devices are one or more integrated circuits, such as an ASIC.

The semiconductors or active electronics include transmit and/or receive circuits for ultrasound scanning with the acoustic array of elements 135. For example, a plurality of transmit circuits are provided as semiconductors chips, a plurality of receive circuits are provided as semiconductor chips, and a controller is provided as a semiconductor chip. The transmit components are separate from or may be integrated with the receive components. Transmit components include high voltage pulsers, filters, memories, delays, phase rotators, multipliers, combinations thereof or other now known or later developed transmit beamformer component. The receive components include filters, amplifiers, delays, summers, combinations thereof or other now known or later developed receive beamformer component. Since receive beamformer components may operate at lower voltages than the transmit components, the receive and transmit components are separate devices (e.g., separate chips or integrated circuits), but a combination device for the transmit and receive operation may be provided. The integrated circuit chip 170 includes all or part of a transmit beamformer, pulsers, receive beamformer, amplifiers, phase rotators, delays, summers, and/or other active electronics used for ultrasound scanning.

The semiconductor chip includes input/output (I/O) pads. The semiconductor chip includes I/O conductors exposed on a largest surface. In alternative embodiments, the pads exit the chip alongside edges and are routed by wire bond or flexible circuit to a distribution on the largest surface. The I/O pads are conductors formed on the chip 170. Cu pillars, electrodes, traces, vias, or other conductive structures may be used for the input/output pads.

The flexible circuit material layer 160 is bonded to the chip 170, such as with flip chip mounting. Epoxy or other bonding material holds the flexible circuit material layer 160 to the integrated circuit chip 170 at the joints 175. The bonding material may additionally form an electrical connection between the input/output pads of the chip and the pads or vias of the flexible circuit material layer 160. For example, an anisotropic conductive film (ACF) or solder is used. In one embodiment, Cu pillar bump joints (e.g., Sn—Ag—Cu composition) with solder caps are used. The chip 170 is placed face-down on the flexible circuit material layer 160. The joints 175 are formed to the pads (cap of Cu pillar bump joints) by high temperature reflow to melt the solder cap, such as a temperature >250° C. Other connections for physical and/or electrical connection may be used, such as asperity contact with an epoxy bond.

FIG. 1 shows an embodiment where two or more tiled chips 170 connect with the flexible circuit material layer 160 but to different tiles 162 due to the slit 400. In one embodiment, a single chip 170 is used so connects to all tiles 162 or a single sheet of flex where tiling is not used. A larger number of acoustic elements 135 and corresponding aperture result in a larger sized chip 170 to handle the acoustic signals. A larger chip 170 is more expensive since the larger chip has more chances to have defects during semiconductor processing. To reduce the size of the chip 170, two or more chips 170 are tiled with a same or different tiling (footprint, shape, and/or orientation) as the tiles 162 of the flexible circuit material layer 160.

The I/O of the chip 170 electrically connects to the transducer elements 135. The transducer elements 135 separately electrically connect to the integrated circuit chip 170 through kerfed portions of the dematching layer 140 and vias in the flexible circuit material layer 160. An electrically separate path is provided from the integrated circuit chip or chips 170 to each element 135. A ground return path connects from the integrated circuit chip or chips 170, through the flexible circuit material layer 160, and through the dematching layer 140 to the ground return layer 150.

Figure 9:
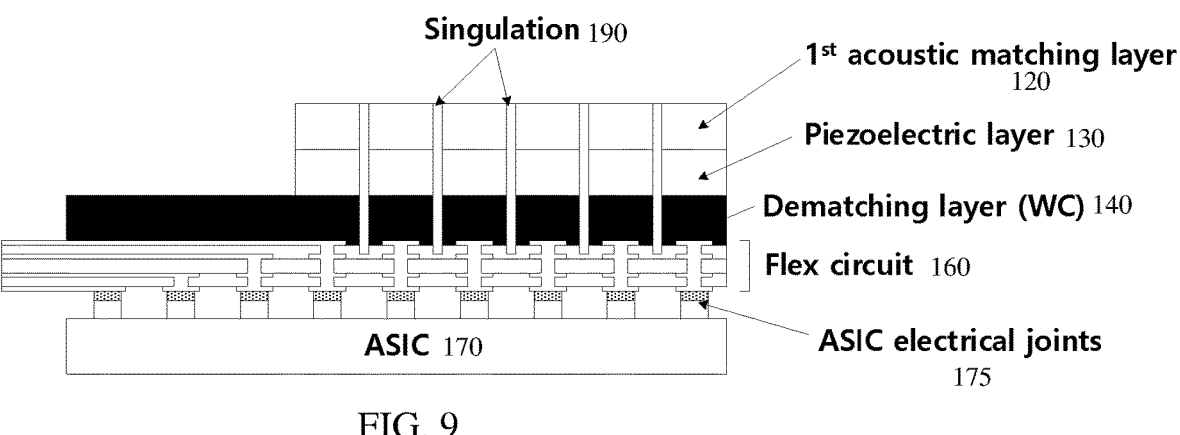

FIG. 9 is a flow chart of one embodiment of a method for forming an acoustic transducer. The ground path connects through an extended size dematching layer, and/or flexible circuit material layer is tiled.

The method forms the array system of FIG. 1 or another array system. The method is implemented as a manufacturing of the array system and/or probe. A technician or robot stacks and aligns, such as using guideposts or a frame. An oven, iron, induction solderer, press, and/or wave bath is used to bond or interconnect. A frame, housing, clamp, or holder are used to shape and position in a probe housing.

Additional, different, or fewer acts may be used. For example, act 500 bonds flex without tiling. As another example, act 540 is not performed. In another example, acts for adding matching layers, lens, or other probe components are provided. In yet another example, testing of the components or parts, sub-assembly, and/or entire assembly is provided. The acts are performed in the order shown or other orders.

Figure 6:
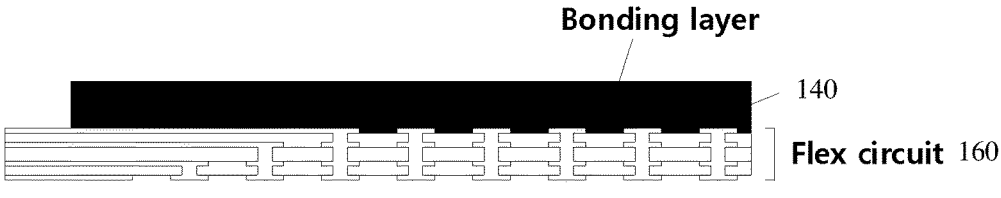
FIG. 6-11 illustrate stages of formation in the method of FIG. 5.

In act 500, tiles of flexible circuit material are bonded to a dematching layer 140. For example, separate sheets of the flexible circuit material are bonded in a same plane to different parts of the dematching layer 140 (see FIG. 3). As another example, a sheet of the flexible circuit material having slits 400 forming tiles 162 is bonded to the dematching layer 140 (see FIG. 4). FIG. 6 shows an example of the dematching layer 140 bonded to the flexible circuit material layer 160. The dematching layer 140 is to be bonded to the piezoelectric layer 130, so also acts as a bonding layer for later attachment.

In one embodiment, the dematching layer 140 is electrically connected to the flexible circuit material layer 160 by one of various bonding materials such as epoxy, Ag paste, solder, anisotropic conductive film (AFC), anisotropic conductive paste (ACP), or another approach. ACF/ACP is a composite film/paste, respectively, of base resin (epoxy or acrylic) and conductive balls/beads (polymer core with Ni/Au plating on it) dispersed in the base resin. These materials are placed between the dematching layer 140 and pads of the flexible circuit material layer 160. The conductive balls within the ACF/ACP are captured in between the pads during thermal-compression bonding, providing electrical current path. The flexible circuit material layer 160 provides electrical connections vertically between integrated circuit chips 170 that will be mounted under the flexible circuit material layer 160 in act 510 and acoustic elements 135 that are later formed in act 520 as well as signal routing toward the ultrasound system from the transducer.

Figure 7:
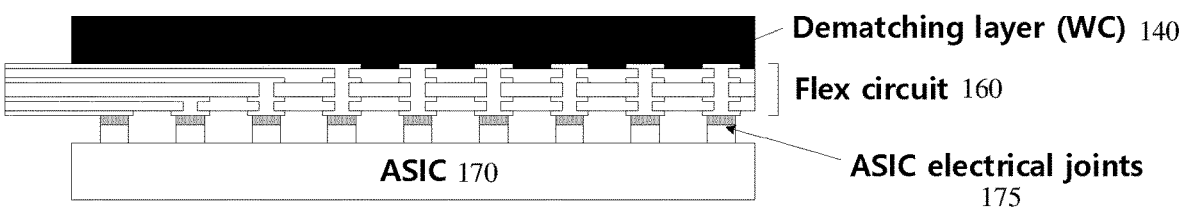

In act 510, one or more semiconductor chips 170 are attached to the flexible circuit material layer 160 opposite the dematching layer 140. The attachment provides physical and electrical connection using application of heat. The semiconductor chip 170 is attached to the flexible circuit material after the bonding of the tiles 162 of the flexible circuit material to the dematching layer 140. FIG. 7 shows an example.

The attachment uses any chip attachment, such as solder reflow or ACF thermal compression bonding. The attachment forms the joints 175 using heat. Since the dematching layer 140 is intrinsically very rigid (>530 GPa in elastic modulus), the dematching layer 140 provides the flexible circuit material layer 160 with dimensional stability for various chip attachment processes. Higher elastic modulus and lower coefficient of thermal expansion (5~6 ppm/° C.) of the dematching layer 140 compared to those of flexible circuit material layer 160 (20 GPa and 18 ppm/° C.) enable suppression of the thermal expansion of the flexible circuit material during various high temperature process (e.g., soldering or ACF bonding), reducing thermal deformation mismatch between the integrated circuit chip 170 and flexible circuit material layer 160. This will also help chip-flex assembly to be flat without any unwanted bending or warpage. In addition, this configuration could reduce the stress caused at the solder joints 175 by thermal deformation mismatch between the integrated circuit chip 170 and flexible circuit material during cooling down after solder reflow at the temperature of ~250° C., improving joint reliability.

In act 520, an array of transducer elements 135 is stacked on the dematching layer 140. The stacking may be of layers before dicing or may be of the array as already diced. Stacking before dicing is described further below.

Figure 8:
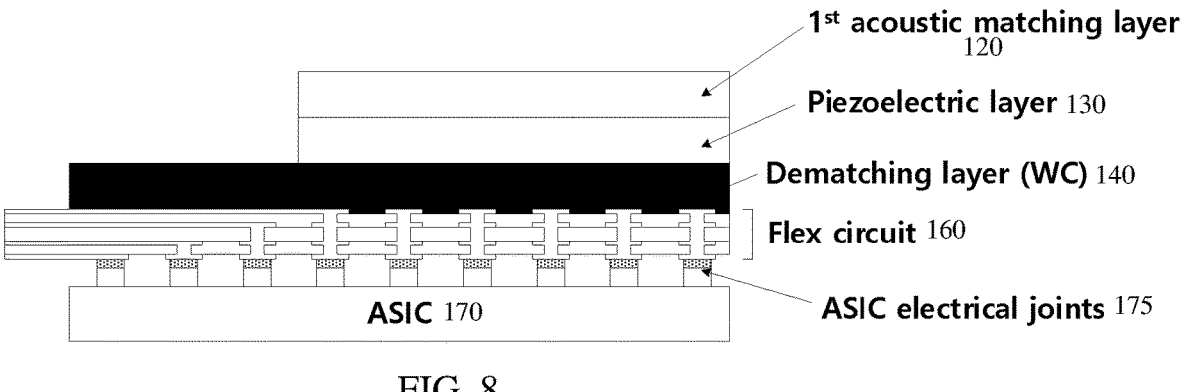

After attaching the integrated circuit chip in act 510 (see FIG. 7), various acoustic layers, such as the PZT layer 130 and the first acoustic matching layer 120 are laminated over the dematching layer 140 as shown in FIG. 8.

The array layers are stacked on the dematching layer. The dematching layer has a larger surface area on a first surface than an area of the largest surface of the array. This results in the dematching layer extending beyond the array as shown in FIGS. 1 and 8.

After laminating or bonding, the elements 135 are formed. The matching layer 120, PZT layer 130, and dematching layer 140 are diced, forming kerfs 190. Any dicing pattern may be used, such as a crisscross or parallel dicing pattern. The dicing creates the array from the singulated elements 190. FIG. 9 shows an example.

In act 530, a ground plane layer 150 is laid on the array. The ground plane layer 150 is a sheet or foil that layers over the elements 135 of the array and onto the dematching layer 140. The extension of the dematching layer 140 is used as a pad for electrical and physical connection to the ground plane layer 150.

Figure 10:
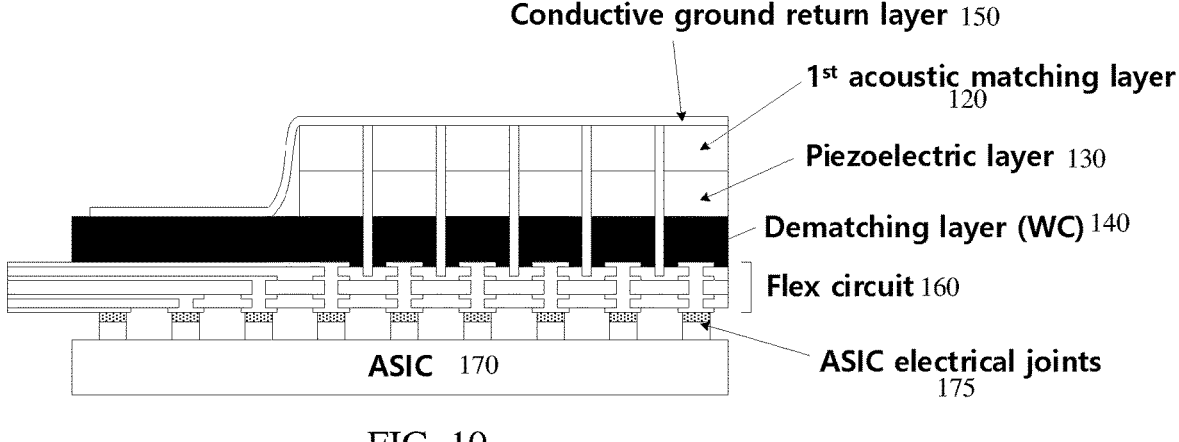

The ground plane layer 150 is conductive and attached over the diced array to provide a ground return path in the transducer. FIG. 10 shows an example. The dematching layer 140 is longer than the piezoelectric layer 130 and the first acoustic matching layer 120. One end of the conductive ground plane layer 150 is terminated over the dematching layer 140 that extends beyond piezoelectric layer 130 and the first acoustic matching layer 120.

In act 540, the ground plane 150 is connected to the dematching layer 140 outside a footprint of the largest surface of the array. Various bonding materials can be used to terminate the ground return layer 150 on the dematching layer 140, such as epoxy, silver paste, and ACP.

The ground plane 150 as laid may be bonded, such as with epoxy, to the array as well. Alternatively, a loose or press fit is provided. The piezoelectric layer 130 and the first acoustic matching layer 120 are an active acoustic aperture to generate ultrasound waves in the transducer's transmit mode and to receive the reflected ultrasound waves in the receive mode.

Figure 11:
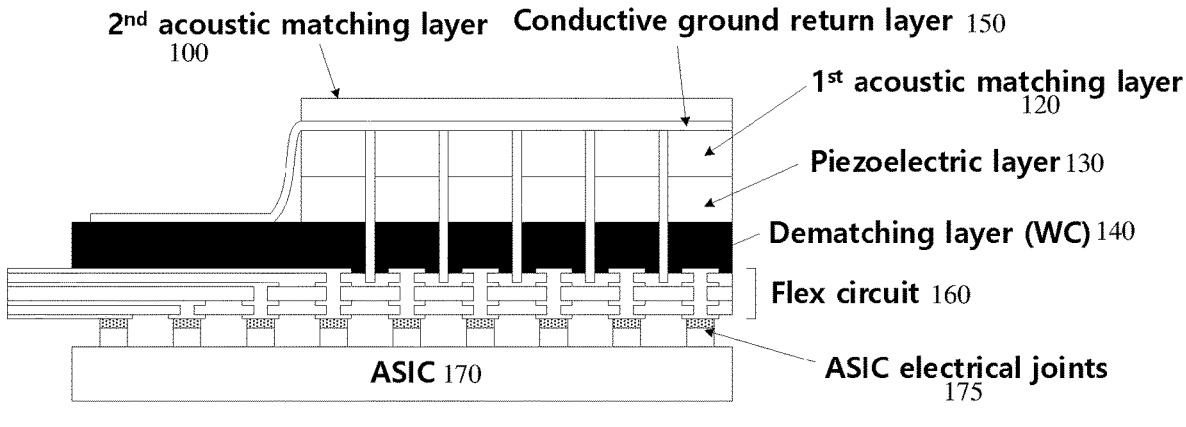

As shown in FIG. 11, the second acoustic matching layer 100 may be stacked or laid on the ground layer 150. The second acoustic matching layer 100 is bonded or press fit to the ground layer 150.

The various bonding or attachments occur in sequence. The PZT layer 130 and first matching layer 120 may be bonded together and to the dematching layer 140 in one bonding step (i.e., at a same time). A lens may be added over the stack.

Independent of the grammatical term usage, individuals with male, female or other gender identities are included within the term.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A multidimensional transducer array system, comprising:
   an acoustic array having transducer elements distributed in a grid over two dimensions in a first area;
   a dematching layer adjacent to the acoustic array, the dematching layer having a second area greater than the first area such that at least a first portion extends beyond a footprint of the acoustic array, the dematching layer being electrically conductive;
   a ground return layer adjacent to the acoustic array on a side opposite the dematching layer, the ground return layer extending onto the dematching layer;
   a flexible circuit material layer adjacent to the dematching layer, the flexible circuit material separated into multiple tiles; and
   an integrated circuit chip connected with the flexible circuit material layer where a ground path connects from the integrated circuit chip, through the flexible circuit material layer, and through the dematching layer to the ground return layer.

2. The multidimensional transducer array system of claim 1, wherein the transducer elements separately electrically connect to the integrated circuit chip through kerfed portions of the dematching layer and vias in the flexible circuit material layer.

3. The multidimensional transducer array system of claim 1, wherein the integrated circuit chip comprises an application specific integrated circuit flip chip mounted to the flexible circuit material layer.

4. The multidimensional transducer array system of claim 1, wherein the transducer elements are separated by kerfs and each comprise a matching layer, a piezoelectric, a kerfed portion of the dematching layer, and a signal electrode, and wherein the ground return layer is free of kerfs and is adjacent to the matching layer.

5. The multidimensional transducer array system of claim 1, wherein the ground return layer comprises a metal sheet that bends at an edge of the acoustic array to connect with the first portion of the dematching layer extending beyond the footprint of the acoustic array.

6. The multidimensional transducer array system of claim 5, wherein the dematching layer has the first portion and a second portion extending beyond the foot print of the acoustic array, and wherein the metal sheet connects with both the first and second portions of the dematching layer.

7. The multidimensional transducer array system of claim 1, wherein the dematching layer comprises tungsten carbide.

8. The multidimensional transducer array system of claim 1, wherein the flexible circuit material layer is separated into multiple tiles as separate sheets in a same plane.

9. The multidimensional transducer array system of claim 1, wherein the flexible circuit material layer is separated into multiple tiles as a sheet having slits formed therein.

10. A transducer array system comprising:
    transducer elements in an array;
    a ground layer distributed over the transducer elements of the array;
    an integrated circuit chip electrically connected to the transducer elements; and
    a dematching layer between the array and the integrated circuit chip, the dematching layer being electrically conductive and having a portion not covered by the array;
    wherein the ground layer extends from over the transducer elements of the array onto the portion of the dematching layer not covered by the array.

11. The transducer array system of claim 10, wherein the dematching layer comprises tungsten carbide.

12. The transducer array system of claim 10, wherein the array has a first area in a plane parallel to an acoustic face, and the dematching layer has a second area parallel with the plane, the second area larger than the first area by an area of the portion.

13. The transducer array system of claim 10, wherein the ground layer comprises a metal sheet that bends at an edge of the array to connect to the dematching layer.

14. The transducer array system of claim 10, further comprising a sheet of flexible circuit material between the dematching layer and the integrated circuit chip, the sheet separated into two or more tiles such that different tiles electrically connect to different ones of the transducer elements.

* * * * *